(12) United States Patent
Sutton et al.

(10) Patent No.: US 6,585,683 B2
(45) Date of Patent: Jul. 1, 2003

(54) TUBING MANAGEMENT MANIFOLD WITH TUBING CAPTURES

(75) Inventors: Thomas B. Sutton, Irvine, CA (US); Susanne M. Roslon, Dana Point, CA (US); Mark S. Cole, Trabuco Canyon, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

(21) Appl. No.: 09/957,191

(22) Filed: Sep. 19, 2001

(65) Prior Publication Data

US 2003/0055387 A1 Mar. 20, 2003

(51) Int. Cl.⁷ .............................................. A61M 1/00
(52) U.S. Cl. ........................................ 604/30; 604/34
(58) Field of Search ........................... 604/30, 34, 131, 604/150, 151, 152, 153; 137/597; 417/477.12, 477.2, 478, 477.1, 477.9, 474

(56) References Cited

U.S. PATENT DOCUMENTS

| | | | |
|---|---|---|---|
| 4,168,707 A | 9/1979 | Douvas et al. | 128/276 |
| 4,369,785 A | 1/1983 | Rehkipf et al. | 128/276 |
| 4,425,116 A | 1/1984 | Bilstad et al. | 604/19 |
| 4,475,904 A | 10/1984 | Wang | 604/27 |
| 4,479,761 A | 10/1984 | Bilstad et al. | 417/395 |
| 4,627,833 A | 12/1986 | Cook | 604/34 |
| 4,713,051 A | 12/1987 | Steppe et al. | 604/30 |
| 4,735,610 A | 4/1988 | Akkas et al. | 604/119 |
| 4,798,580 A | 1/1989 | DeMeo et al. | 604/30 |
| 4,904,168 A | 2/1990 | Covoto et al. | 417/477 |
| 4,921,477 A | 5/1990 | Davis | 604/22 |
| 4,963,131 A | 10/1990 | Wortrich | 604/34 |
| 5,009,641 A | * 4/1991 | Gorton | 604/131 |
| 5,106,366 A | 4/1992 | Steppe | 604/30 |
| 5,267,956 A | 12/1993 | Beuchat | 604/30 |
| 5,464,388 A | * 11/1995 | Merte et al. | 604/153 |
| 5,470,312 A | 11/1995 | Zanger et al. | 604/34 |
| 5,554,113 A | 9/1996 | Novak et al. | 604/30 |
| 5,586,738 A | * 12/1996 | Binelli | 248/73 |
| 5,868,678 A | 2/1999 | Brunner et al. | 600/486 |
| 6,059,765 A | 5/2000 | Cole et al. | 604/500 |
| 6,059,795 A | * 5/2000 | Wallace et al. | 606/123 |

FOREIGN PATENT DOCUMENTS

| | | | | |
|---|---|---|---|---|
| DE | 3705266 A1 | 9/1988 | | A61F/9/00 |
| EP | 0293 081 A1 | 4/1988 | | A61M/1/00 |
| WO | WO 86/07249 | 12/1986 | | A61B/17/00 |

* cited by examiner

Primary Examiner—Brian L. Casler
Assistant Examiner—Matthew F DeSanto
(74) Attorney, Agent, or Firm—Walter A. Hackler; Peter Jon Gluck

(57) ABSTRACT

A tubing management manifold for a surgical instrument console for controlling fluidflow to and from a surgical instrument includes a housing having a front and opposing sides, and sides, for enabling tubing to be disposed therein and across the housing between the opposing sides. Ports, disposed in the housing front are provided for enabling access to the tubing, disposed across the housing, in order to control fluid flow through the tubing. A tubing capture is disposed on one of the opposing sides, aligned with one of said openings and extending outwardly from said housing, for grasping the tubing in order to prevent unwanted dislodgement of the tubing from said housing.

9 Claims, 1 Drawing Sheet

TUBING MANAGEMENT MANIFOLD WITH TUBING CAPTURES

The present invention generally relates to irrigation/aspiration apparatus for surgical procedures and more particularly relates to fluid management apparatus for use with a surgical instrument for endophthalmic surgery.

The removal of cataracts, for example, involves surgery on a normally pressurized eye in which instruments are passed through a small incision at the edge of the cornea in order to access and remove opaque cataract material.

The cataracts may be fragmentized by cutting apparatus, vibratory apparatus, or the like, and the fragments are aspirated from the eye.

In order to maintain normal pressure within the eye, a balanced saline solution is supplied from an elevated chamber, the chamber being elevated to a position to provide proper head, or pressure.

The irrigation and aspiration of fluid through the eye must be carefully monitored and controlled in order to maintain normal pressure within the eye during surgical procedures. An under-pressure may cause distortion of the eye which often may interfere with surgical procedures. Over pressure may cause damage to the eye and in extreme cases, rupture thereof.

As it has been hereinabove noted, pressure in the eye may be controlled by the physical elevation of the chamber of balanced saline solution, which is connected to the surgical instrument. Aspiration fluid, on the other hand, is typically controlled in the eye with a peristaltic pump or the like.

Conventional apparatus includes an instrument console for controlling the flow of fluids. Various devices have been developed for the coordinated flow of fluids and some include a phacocassette, or tubing and management system, which may be disposable or autoclavable, for interconnecting from the various tubes and lines for proper irrigation and aspiration.

A general discussion of the advantages of this type of cassette is set forth in U.S. Pat. No. 4,713,051, which teaches a housing for supporting a portion of irrigation and aspiration tubing, together with a drain bag structured so that all fluid and connections are precisely made to a console by insertion of the cassette thereinto. Thus, the reliability of the fluid connections is enhanced.

Other fluid management apparatus for control of irrigation and aspiration fluid as well as cassettes therefore are discussed in U.S. Pat. Nos. 4,424,116; 4,475,904; 4,479,761; 4,627,833; 4,735,610; 4,798,580; 4,904,168; 4,963,131; 5,106,366; 5,470,312 and 6,059,765.

The last hereinabove referenced namely, U.S. Pat. No. 5,470,312, teaches a chamber and diaphragm arrangement for improving response time to pressure variations in an aspiration line while a surgical instrument and is incorporated herewith entirely by this specific reference thereto.

A chronic problem with the use of hereinbefore tubing management systems, or cassettes, is the maintenance of tubing displaced in the cassettes. Slots or openings generally provided in the cassette aligned tubing therewithin for access by plungers and the like when installed on a console, the plungers being actuated to effect flow control through the tubing in the cassette. Proper alignment must be maintained in order that fluidflow through the tubing can be precisely controlled. Unfortunately, handling of the cassette or manifold, in combination with applied pressure to the tube to control flow therethrough has a tendency to dislodge or misalign the tubing within the manifold.

The present invention provides for a tubing management manifold which includes tubing captures to insure tubing placement within the manifold and prevent unwanted dislodgment or misalignment of the tubing from and within the manifold.

SUMMARY OF THE INVENTION

A tubing management manifold in accordance with the present invention for surgical instrument console for controlling fluidflow to and from a surgical instrument generally includes a housing having a front and opposing sides. Openings disposed, in each of the opposing sides are provided for enabling the tubing to be disposed between and across the opposing sides.

Ports disposed in the housing front enable access to the tubing disposed across the housing in order to control fluidflow through the tubing. This occurs when the tubing management manifold is installed in a corresponding console having solenoids or actuators for contacting and compressing the tubing through the ports.

A tubing capture is disposed on one of the opposing sides and aligned with one of the openings is provided for grasping the tubing in order to prevent unwanted dislodgement of the tubing from the housing. Preferably, the capture extend outwardly from the housing in order to minimize housing size and enable easy access to the tubing through the ports.

Preferably, the housing has an open back and the openings therein subtend a back edge of the opposing sides. The tubing capture includes an open side for enabling transverse placement of the tubing along a longitudinal axis of the tubing capture.

A first internal transverse flange is provided in the caputure having a bore therethrough of a diameter for enablign the tubing to pass therethrough and a slot in the first flange enables the tubing to be transversely urged into the bore. The slot has a width smaller than the tubing diameter and accordingly, after being pushed therepast, the tubing resides in the flange bore.

Preferably a second internal transverse flange is provided and disposed at a spaced apart distance from the first flange with a second flange having a bore therethrough of a diameter for enabling the tubing to pass therethrough and a slot in the second flange enables the tubing to be transversely urged into the second flange bore. Second flange slot also has a width smaller than a tubing diameter which prevents withdrawal of the tubing of the second flange bore without positive force being applied thereto.

The combination of flanges in a spaced apart relationship provides for a secure holding of the tubing in its relationship across the housing, and thus, prevents unwanted dislodgement of the tubing from the housing.

The tubing capture longitudinal axis may be disposed approximately at a right angle to the opposing sides or at an acute angle, for example 40°.

The present invention also includes the combination of the tubing management manifold hereinabove described in combination with the tubing.

The present invention may further include a tubing coupler disposed in one end of the tubing for joining the tubing with a second tubing with the coupler having an outside diameter smaller than the tubing outside diameter and the tubing capture includes a second internal transverse flange having a bore therethrough of a diameter enabling the coupler to pass therethrough and a slot in the second flange for enabling the coupler to be transversely urged into the second flange bore. The second flange slot in the embodiment has a width smaller than the coupler outside diameter.

BRIEF DESCRIPTION OF THE DRAWINGS

The advantages and features of the present invention will be better understood by the following description when considered in conjunction with the accompanying drawings in which.

DETAILED DESCRIPTION

Figure 1:
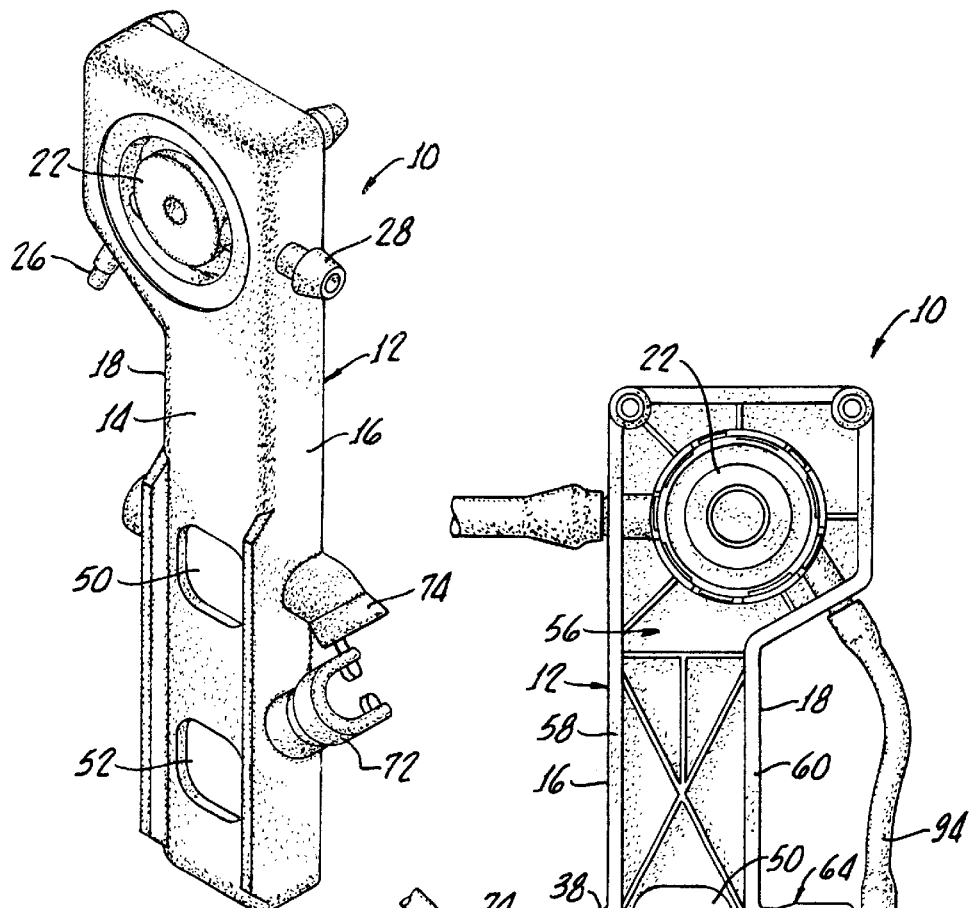
FIG. 1 is a perspective view of the tubing management manifold in accordance with the present invention generally showing housing openings in opposing sides of the housing for enabling tubing to be disposed therein and across the housing and ports disposed in the housing front for enabling access to the tubing. Also shown are tubing captures disposed on sides of the housing and extending outwardly therefrom for grasping the tubing in order to prevent unwanted dislodgement of the tubing from the housing.
Figure 2:
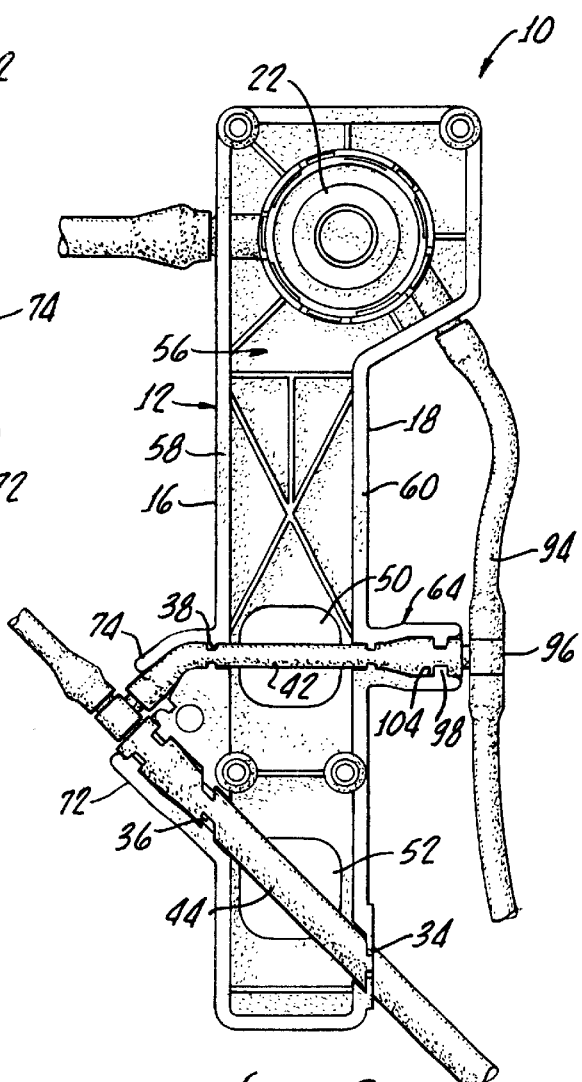
FIG. 2 is a plan view of the back of the housing along with tubing held in an operative relationship with housing by the tubing captures.

With reference to FIGS. 1 and 2, there is shown a tubing management manifold 10 for a surgical instrument, console (not shown) for controlling fluidflow to and from a surgical instrument (not shown).

The manifold 10 generally includes a housing 12 having a front 14 and opposing sides 16, 18. The housing 10 also includes a chamber 22 having an aspiration inlet 26 and an outlet 28. While not part of the present invention, this structure of the housing is more clearly defined in U.S. Pat. No. 6,059,765 which is incorporated herewith in its entirety by the specific reference thereto.

The housing 10 may be formed from any suitable material such as a plastic, suitable for surgical apparatus. Openings 32, 34, 38 disposed in each of the opposing sides 16, 18 enable tubing 42, 44 to be disposed across ports 50, 52 which enable access to the tubing 42, 44 in order to control fluid flow through the tubing 42, 44. Fluid flow is effected through the use of plungers (not shown) or the like which are actuated to compress the tubing 42, 44. The plungers are present in a console (not shown) for receiving the housing 10. Control of this type is set forth in U.S. Pat. No. 5,470,312 which is incorporated herewith in its entirety by these specific references thereto.

As shown in FIG. 2, the housing 10 has an open back 56 and the openings 32–38 subtend back edges 58, 60 of the sides 16, 18. A tubing capture 64 is disposed, and preferably molded, into the side 18 of the housing 10 and aligned with the opening 32. The capture 64 extends outwardly from the housing 10 for grasping the tubing 42 in order to prevent unwanted dislodgment of the tubing 42 from the housing 10. Similarly, a capture 72 protrudes from housing side 16 and is aligned with the opening 36 in the side edge 58. A capture 74 also protrudes from the housing side 16 and is aligned with the opening 38.

The description of the capture 64 applies to the captures 72, 74 and for the sake of brevity detailed descriptions of the capture 72, 74 will not be presented.

Figure 3:
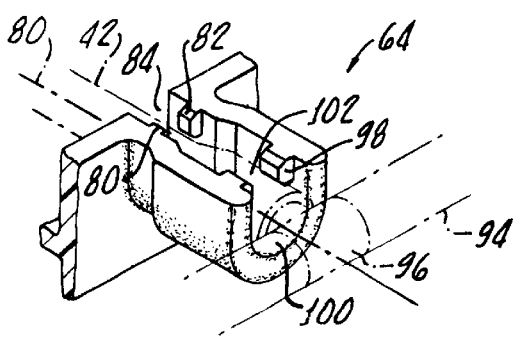
FIG. 3 is an enlarged view of a capture in accordance with the present invention.

As most clearly shown in FIGS. 2 and 3, the tubing capture 64 includes a first internal transverse flange 80 having a bore 82 therethrough of a diameter for enabling the tubing 42 to pass therethrough. A slot 84 in the first flange 80 enables the tubing 42 to be transversely urged into the bore 82 along a longitudinal axis 88 of the capture 84. The slot 84 has a width smaller than a tubing 42 diameter. Accordingly, once the tubing 42 resides in the bore 82 of the flange 80, force must be applied in order to dislodge the tubing 42 from the housing 12.

In order to accommodate the multiple tubing and interrelationship there between, the capture 64 may be disposed at a 90° angle to the side 18 whereas the capture 72 may be disposed at a 45° angle to the side 16. It should be appreciated that any angular relationship may be utilized to accommodate specific matrices.

Tubing 42 may be coupled to aspiration tubing 94 by means of a tubing couple 96. In this instance, the capture 64 may include a second flange 98 having a bore 100 therethrough. The coupler 96 has an outside diameter smaller than an outside diameter of the tubing 42 and the bore 100 is sized to accommodate the couple 96 outside diameter. The slot 102 in the second flange 98 enables the coupler to be transversely urged into the second flange bore 100. The second flange slot 102 has a width smaller than the coupler 96 outside diameter to maintain retention of the coupler 96 and tubing so that unwarranted dislodgment of the couple 96 tubing 42 arrangement, does not occur.

Further, the longitudinal movement of the tubing 42 transverse to the housing 12 and along the capture access 80 is inhibited by a grasping of the couple 96 between a tubing end 104 and the couple 96.

Although there has been hereinabove described a tubing management manifold with tubing captures in accordance with the present invention, for the purpose of illustrating the manner in which the invention may be used to advantage, it will be appreciated that the invention is not limited thereto. Accordingly, any and all modifications, variations, or equivalent arrangements which may occur to those skilled in the art should be considered to be within the scope of the invention as defined in the appended claims.

What is claimed is:

1. A tubing management manifold for a surgical instrument console for controlling fluidflow to and from a surgical instrument, the manifold comprising:

a housing having a front and opposing sides;

openings, disposed in each of said opposing sides, for enabling tubing to be disposed therein and across the housing between said opposing sides;

ports, disposed in the housing front, for enabling access to the tubing, disposed across the housing, in order to control fluidflow through the tubing; and an open sided tubing capture disposed on one of said opposing sides, aligned with one of said openings and extending outwardly from said housing, for grasping the tubing in order to prevent unwanted dislodgement of the tubing from said housing, said tubing capture including a first internal transverse flange having a bore therethrough of a diameter for enabling said tubing to pass therethrough and a slot in the first flange for enabling said tubing to be transversely urged into said bore, said slot having a width smaller than a tubing outside diameter; and a second internal transverse flange disposed at a spaced apart distance from the first flange, the second flange having a bore therethrough of a diameter for enabling said tubing to pass therethrough and a slot in the second flange for enabling said tubing to be transversely urged into the second flange bore, the second flange slot having a width smaller than the tubing diameter.

2. The manifold according to claim 1 wherein said housing has an open back and the openings subtend a back edge of said opposing sides.

3. The manifold according to claim 1 wherein the tubing capture longitudinal axis is disposed approximately at a right angle to the opposing sides.

4. The manifold according to claim 1 wherein the tubing capture longitudinal axis is disposed approximately 45° angle to the opposing sides.

5. A tubing management manifold for a surgical instrument console for controlling fluidflow to and from a surgical instrument, the manifold comprising:

a housing having a front and opposing sides;

tubing;

openings, disposed in each of said opposing sides, for enabling the tubing to be disposed therein and across the housing between said opposing sides;

ports, disposed in the housing front, for enabling access to the tubing, disposed across the housing, in order to control fluidflow through the tubing; and an open sided tubing capture disposed on one of said opposing sides, aligned with one of said openings and extending outwardly from said housing, for grasping the tubing in order to prevent unwanted dislodgement of the tubing from the said housing, said tubing capture including a first internal transverse flange having a bore therethrough of a diameter for enabling said tubing to pass therethrough and a slot in the first flange for enabling said tubing to be transversely urged into said bore, said slot having a width smaller than a tubing outside diameter; and a second internal transverse flange disposed at a spaced apart distance from the first flange, the second flange having a bore therethrough of a diameter for enabling said tubing to pass therethrough of a diameter for enabling said tubing to be transversely urged into the second flange bore, the second flange slot having a width smaller than the tubing diameter.

6. The manifold according to claim 5 further comprising a tubing coupler, disposed in one end of said tubing, for joining said tubing with second tubing, the coupler having an outside diameter smaller than the tubing outside diameter and said tubing capture includes a second internal transverse flange disposed at a spaced apart distance from the first flange, the second flange having a bore therethrough of a diameter for enabling the coupler to pass therethrough and a slot in the second flange for enabling the coupler to be transversely urged into the second flange bore, the second flange slot having a width smaller than the coupler outside diameter.

7. The manifold according to claim 6 wherein the tubing capture longitudinal axis is disposed approximately at a right angle to the opposing sides.

8. The manifold according to claim 6 wherein the tubing capture longitudinal axis is disposed approximately at a 45° angle to the opposing sides.

9. The manifold according to claim 5 wherein said housing has an open back and the openings subtend a back edge of said opposing sides.

* * * * *